(12) United States Patent
Cecere et al.

(10) Patent No.: US 10,004,600 B2
(45) Date of Patent: Jun. 26, 2018

(54) DEVICE FOR SOFT TISSUE SUPPORT AND METHOD FOR ANCHORING

(71) Applicant: THE ROYAL INSTITUTION FOR THE ADVANCEMENT OF LEARNING/MCGILL UNIVERSITY, Montreal (CA)

(72) Inventors: Renzo Cecere, Town of Mont Royal (CA); Rosaire Mongrain, Montreal (CA); Toufic Azar, Montreal (CA); Jorge Angeles, Montreal (CA); Jozsef Kovecses, Saint-Bruno (CA)

(73) Assignees: Renzo Cecere, Town of Mont Royal (CA); Rosaire Mongrain, Montreal (CA); Toufic Azar, Montreal (CA); Jorge Angeles, Montreal (CA); Jozsef Kovecses, Saint-Bruno (CA)

( * ) Notice: Subject to any disclaimer, the term of this patent is extended or adjusted under 35 U.S.C. 154(b) by 0 days. days.

(21) Appl. No.: 14/398,247

(22) PCT Filed: May 2, 2013

(86) PCT No.: PCT/CA2013/050341
§ 371 (c)(1),
(2) Date: Oct. 31, 2014

(87) PCT Pub. No.: WO2013/163762
PCT Pub. Date: Nov. 7, 2013

(65) Prior Publication Data
US 2015/0127091 A1 May 7, 2015

Related U.S. Application Data

(60) Provisional application No. 61/641,498, filed on May 2, 2012.

(51) Int. Cl.
*A61F 2/24* (2006.01)
*A61F 2/848* (2013.01)

(52) U.S. Cl.
CPC .......... *A61F 2/2442* (2013.01); *A61F 2/2445* (2013.01); *A61F 2/848* (2013.01); *A61F 2220/0016* (2013.01); *A61F 2250/001* (2013.01)

(58) Field of Classification Search
CPC .... A61F 2/2442; A61F 2/2445; A61F 2/2448; A61F 2/848; A61F 2220/0016
See application file for complete search history.

(56) References Cited

U.S. PATENT DOCUMENTS

| 6,602,288 | B1 | 8/2003 | Cosgrove et al. |
| 7,297,150 | B2 | 11/2007 | Cartledge et al. |

(Continued)

OTHER PUBLICATIONS

International search report and written opinion for PCT application PCT/CA2013/050341 filed May 2, 2013, from which the present application is a national phase entry.

*Primary Examiner* — Dinah Baria

(57) ABSTRACT

A device for supporting soft tissue includes a tubular body and is constituted of a sequence of compliant portions and anchoring portions. The anchoring portions each include anchor members adapted to penetrate into soft tissue. The compliant portions each include deformable members extending between ends of the compliant portion, at least one of a distance and orientation between said ends being adjustable by application of a force on the tubular body. The tubular body includes a ring-like shape reached at least by deformation of the compliant portions, the ring-like shape having the anchor members of the anchoring portions protruding circumferentially along a direction defined by a vector having a component being at least tangential to the curve of the ring-like shape, for the anchor members to (Continued)

penetrate the soft tissue. A method for anchoring the device to soft tissue is also provided.

11 Claims, 12 Drawing Sheets

(56) References Cited

U.S. PATENT DOCUMENTS

| | | | |
|---|---|---|---|
| 8,202,315 B2 | 6/2012 | Hlavka et al. |
| 8,262,724 B2 | 9/2012 | Seguin et al. |
| 8,277,502 B2 | 10/2012 | Miller et al. |
| 8,343,173 B2 | 1/2013 | Starksen et al. |
| 8,357,195 B2 | 1/2013 | Kuehn |
| 8,382,653 B2 | 2/2013 | Dubi et al. |
| 8,382,829 B1 | 2/2013 | Call et al. |
| 8,454,656 B2 | 6/2013 | Tuval |
| 8,518,107 B2 | 8/2013 | Tsukashima et al. |
| 8,728,097 B1 | 5/2014 | Sugimoto et al. |
| 8,747,462 B2 | 6/2014 | Hill et al. |
| 2003/0225420 A1 | 12/2003 | Wardle |
| 2004/0167620 A1 | 8/2004 | Ortiz et al. |
| 2004/0236419 A1 | 11/2004 | Milo |
| 2006/0020336 A1 | 1/2006 | Liddicoat |
| 2007/0080188 A1 | 4/2007 | Spence et al. |
| 2007/0244553 A1 | 10/2007 | Rafiee et al. |
| 2007/0250161 A1* | 10/2007 | Dolan .................. A61F 2/2445 623/2.11 |
| 2008/0243150 A1 | 10/2008 | Starksen et al. |
| 2008/0281411 A1 | 11/2008 | Berreklouw |
| 2009/0259307 A1 | 10/2009 | Gross et al. |
| 2010/0076549 A1 | 3/2010 | Keidar et al. |
| 2010/0121433 A1 | 5/2010 | Bolling et al. |
| 2011/0118819 A1* | 5/2011 | Contiliano ................ A61F 2/91 623/1.15 |
| 2011/0166649 A1* | 7/2011 | Gross .................... A61F 2/2445 623/2.36 |
| 2012/0053687 A1 | 3/2012 | Migliazza et al. |
| 2012/0123531 A1 | 5/2012 | Tsukashima et al. |
| 2012/0296160 A1 | 11/2012 | Hill et al. |
| 2012/0310330 A1 | 12/2012 | Buchbinder et al. |
| 2014/0148849 A1 | 5/2014 | Serina et al. |
| 2014/0148898 A1 | 5/2014 | Gross et al. |

* cited by examiner

DEVICE FOR SOFT TISSUE SUPPORT AND METHOD FOR ANCHORING

CROSS-REFERENCE TO RELATED APPLICATION

The present disclosure claims the benefit of U.S. provisional patent application No. 61/641,498, filed on May 2, 2012, the content of which is incorporated herein by reference.

FIELD OF THE INVENTION

The present disclosure relates generally to a device for soft tissue support, specifically but not exclusively for heart tissue support such as the mitral valve annulus. The present disclosure also relates to a tool for delivering a soft tissue support device.

BACKGROUND OF THE INVENTION

In a healthy heart, a heart valve allows blood flow generally in one direction. In some conditions, such as mitral valve regurgitation, a valve may be prevented from closing properly thereby causing blood to flow backwards as well as in the intended direction. This can increase the workload on the heart and if left untreated can lead to irreversible heart damage.

Existing methods of mitral valve repair include open heart surgery to attach a circular or semi-circular prosthetic ring in order to reduce the size of the annulus, from which the heart valve's leaflets are supported, to bring closer together the leaking valve leaflets. However, there are significant disadvantages associated with open heart surgery including longer recovery times for the patient, increased chance of infection, and unsuitability for high risk patients.

A percutaneous method of treating this condition would circumvent the disadvantages associated with open heart surgery. However, a percutaneous approach offers additional challenges due to constraints such as anatomy and the dynamic nature of a beating heart. For example, blood flow is present which may not allow direct imaging of the valve and the implant. Also, movement of the annulus can create instability between the implant and the tissue. There must also be an appropriate delivery method for the device which can securely attach the device to the tissue.

Therefore, there is a need for an improved device for supporting soft tissue and a tool for delivering such a device.

SUMMARY OF THE INVENTION

The embodiments of the present invention reduce the aforesaid difficulties and disadvantages.

Therefore, in accordance with the present disclosure, there is provided a device for supporting soft tissue, the device comprising: a tubular body and is constituted of a sequence of compliant portions and anchoring portions, the anchoring portions each comprising at least one anchor member adapted to penetrate into soft tissue, the compliant portions each comprising at least one deformable member extending between ends of the compliant portion, at least one of a distance and orientation between said ends being adjustable by application of a force on the tubular body; the tubular body comprising a ring-like shape reached at least by deformation of the compliant portions, the ring-like shape having the anchor members of the anchoring portions protruding circumferentially along a direction defined by a vector having a component being at least tangential to the curve of the ring-like shape, for the retaining members to penetrate the soft tissue.

Further in accordance with the present disclosure, the at least one anchor member has a finger having a free end for protruding into the soft tissue in use and a base end connected to a remainder to the tubular body.

Still further in accordance with the present disclosure, the anchor member is shaped as a fir tree, with the free end having a pointy shape, and retaining members projecting laterally from the fingers.

Still further in accordance with the present disclosure, two said anchor members are provided for each said anchoring portion.

Still further in accordance with the present disclosure, the anchoring portions each comprise tubular bands at opposite ends, and at least deformable strut between the tubular bands, the at least one anchor member projecting from one said tubular bands.

Still further in accordance with the present disclosure, the elongated body comprises a plurality of the compliant portions and the anchoring portions, said compliant portions and anchoring portions being alternately positioned along the length of the tubular body.

Still further in accordance with the present disclosure, the at least one deformable member is a longitudinal strip of undulating pattern.

Still further in accordance with the present disclosure, a plurality of the strips extend along the compliant portion, and at least one ring transversely connecting the strips and tubularly aligned with the tubular elongated body.

Still further in accordance with the present disclosure, the tubular body has a length ranging between 7.0 and 13.0 cm.

Still further in accordance with the present disclosure, the elongated body has a diameter ranging between 2.0 and 4.0 mm in a non-deformed linear configuration.

In accordance with a further embodiment, there is provided a method for anchoring an implant to an annular structure of soft tissue comprising: positioning an implant in a ring-like shape along the annular structure of soft tissue; and rotating the implant in its ring-like shape for the implant to move along the annular structure; whereby anchoring members on the implant penetrate into the soft tissue for anchoring the implant into the annular structure.

Further in accordance with the present disclosure, the implant percutaneously shaped from a linear shape into the ring-like shape prior to positioning.

Still further in accordance with the present disclosure, a guidewire is positioned with a portion being along the annular structure, and wherein shaping the implant comprises moving the implant in the linear shape onto the guidewire to reach the ring-like shape at said portion.

Still further in accordance with the present disclosure, the dimensions of the implant are adjusted in its ring like shape as a function of the annular structure Still further in accordance with the present disclosure, the dimensions are reduced to reduce the dimensions of the annular structure.

Still further in accordance with the present disclosure, rotating the implant comprises inserting a deployment tool through a center of the implant in its ring-like shape, deploying the deployment tool to engage the ring-like shape, and rotating the deployment tool thereby rotating the implant.

Still further in accordance with the present disclosure, positioning the implant comprises positioning a guidewire with a portion being along the annular structure, and moving the implant onto the guidewire to reach the ring-like shape at said portion.

Still further in accordance with the present disclosure, the method is performed to install the implant on the annulus of the mitral valve.

From a another aspect, there is provided a device for supporting soft tissue, the device comprising an elongate body having at least one compliant portion (hereinafter referred to as "compliant portion') and at least one anchoring portion. Advantageously, the length of the elongate body can be adjusted by means of the at least one compliant portion such as by compressing/contracting or expanding the at least one compliant portion. Also by means of the compliant and the anchoring portions, the elongate body can be bent so as to be configurable between a linear configuration/state and a shaped configuration/state. Advantageously, the device can be delivered to the desired location in situ through a small tube such as a catheter or cannula (i.e. percutaneously) while in the linear state. The device can then be shaped by means of the compliant portions in order to adapt the device to support the soft tissue. The device can be placed into an appropriate shape or form for the soft tissue to be supported.

The compliant portion can also be termed a flexible or adjustable portion. It can have any configuration allowing the bending of the elongate body, as well as its re-sizing. By a shaped configuration is meant that the elongate body is curved into a non-linear arrangement such as a substantially ring-like or other curved configuration. By substantially ring-like is meant a complete ring in which free ends of the elongate member meet, or a partial ring in which the free ends do not meet, i.e. there is a gap between the free ends of the elongate member. The shaped configuration can include a round, oval, "C" or "D"-shape, saddle or any other shape.

In an embodiment, the soft tissue is heart tissue and the device can be used as an annuloplasty ring for mitral valve repair. The device can be delivered to the heart while in its linear state, shaped according to the mitral annulus and attached to the mitral annulus by means of the anchoring portion. Once attached, the length of the compliant portion can be shortened by means of the compliant portion in order to reduce the circumference of the mitral annulus which can allow the mitral valve to close properly. Alternatively, the device can be lengthened by stretching the compliant portion. The length of the device and/or compliant portion can be adjusted before or after attachment to the soft tissue. The adjustment function can be performed by a wire or other element extending through the device or attached to the device, for example, similar to a purse string effect or lasso mechanism.

The at least one anchoring portion comprises at least one anchor member for penetrating the soft tissue. The at least one anchor member has a body having a free end for protruding into the soft tissue in use and a base end connected to the elongate body. The base end is preferably moveably connected to the elongate body so that the anchor member can move between an undeployed position and a deployed position. In the deployed position, the anchor member is configured to penetrate the soft tissue in use.

The anchor member is shaped for protruding into the soft tissue in use. The free end can be narrower than the base end to facilitate piercing the soft tissue. The anchor member can be chevron shaped or arrow shaped, or any other suitable shape. The dimensions of the anchor member can be selected according to the intended use, for example, the thickness of the soft tissue which it will protrude. The direction of the anchor can be tangential, or at any angle with the plane defined by the valve.

The elongated body comprises a contact surface for contacting the soft tissue in use, and the at least one anchor member is provided or formed on the contact surface. The at least one anchor member can be part of the contact surface and formed so that it lies on the same plane as the elongate member when the elongate member is linearly configured. This can be considered as an undeployed position of the anchor member. The anchor member can be moved to a deployed position in which the anchor member or the free end of the anchor member protrudes away from the contact surfaces. The deployed position can be initiated such as by bending or curving the elongate body, for example into a partial or complete ring shape. For the anchor member to protrude, a bending moment must be transmitted along the implant. Both compliant and anchoring portions must transmit that moment. The degree of bending may be equally distributed between both portions.

The anchor member can be deployed by other means, such as by having a resilient bias to the deployed position (i.e. extending away from the elongate body) and being held in the undeployed position by a cover such as a sheath. Removal of the cover will then deploy the anchor member by causing the anchor member free end to move away from the elongate body. In one embodiment, the anchor member and the anchoring portion are one-piece and the anchor member is formed by etching or cutting, such as by laser, the contact surface.

In another embodiment, the anchor members can be formed of nitinol and deployed using the shape memory effect of nitinol such that at normal internal body temperature the anchor members recover their protruded form.

A plurality of anchor members can be provided which are oriented in relation to the elongate body in substantially the same direction. In other words, the anchor members point to substantially the same direction. The plurality of anchor members can be arranged in rows along the elongate body, or in any other arrangement. Advantageously, due to the directionality of the anchor members, they can be caused to pierce the soft tissue at the same time when the device is moved along the soft tissue surface in the direction which the free end is pointing. When the device is in a curved configuration (e.g. ring-like), the device can be rotated against the soft tissue surface in the direction of the anchor member free ends in order for the free ends to penetrate the soft tissue. A skilled person will appreciate that the user may also need to impart some pressure on the device in order for the free ends to pierce the soft tissue. Advantageously, the device can be retracted by pulling in the reverse direction of insertion.

The device may further comprise a retaining element for retaining the anchor member in the soft tissue. The retaining element can be part of the anchor member, or on any other part of the device such as another part of the anchoring portion or the compliant portion. In one embodiment, the retaining element comprises protrusions on at least a portion of a surface of the anchor member which can be scallop-shaped or scale-like. They can be any other suitable shape for resisting the pulling out of the device from the soft tissue. The anchors can be coated with fixation and adhesive promoting microscales such as porcupine quills or the like.

The elongate body can be tubular. Advantageously, by providing a tubular elongate body, the device has suitable structural integrity and mechanical properties for bending without yielding. The weight of the elongate body can be kept low by providing a hollow tube. Preferably, the diameter of the elongate body is small enough to be delivered through a tube such as a catheter.

The elongate body can include a plurality of compressible and anchoring portions, said portions being alternately positioned along the length of the elongate body, or in any other configuration. The elongate body or the anchoring portions and compliant portions may include spacers or the like between the portions.

The at least one compressible section can comprise at least one flexible element. When the compressible section is adjacent two anchoring portions, one on either side of the compressible section, the flexible element can extend between the adjacent anchoring portions to connect or bridge the two anchoring portions together. The at least one flexible element can comprise a coil(s) of material, strip(s) of material or any other suitable shape or form to allow bending, compressing/shortening and elongating/lengthening such as a concertina form. The strip(s) can be substantially sinusoidal (wavy'), zigzag shaped or the like. The strips can be substantially parallel to one another.

Many permutations of the arrangement of the anchor members and flexible elements on the elongate body are possible. For example, a segment of the elongate body which has an anchor member may also include an oppositely facing flexible element. In one embodiment, the elongate body is a tubular structure, and the advantage of having a flexible or deformable element on the opposite segment of the tube as the anchor member facilitates the protrusion or 'pop-out' of the anchor member when that segment of the tubular structure bends.

Preferably, the elongate body is one-piece, or the anchoring portion is one-piece, or the compliant portion is one-piece. Advantageously, the various portions and elements can be formed by cutting or etching a single tube, such as by using a laser.

The device or components of the device can be made of any biomaterial. By biomaterial is meant any biocompatible material which is suitable for implantation in a body and has the requisite mechanical properties for the intended use. Suitable materials include, but are not limited to, stainless steel 316L, titanium or titanium alloys, such as Nitinol or Ti—Al—V, cobalt chromium alloys, other metallic alloys, polymers, composites. In a preferred embodiment, the device is a single tube of Stainless Steel 316L which is laser cut/etched to form the compressible and anchoring portions. Alternatively, the device can be made from different components/materials joined together. Also, the device or parts of the device can have a coating for promoting cell growth to aid fixation of the device to the tissue and for improving biocompatibility by minimizing hemolysis, blood shear and clot formation.

Optionally, the device can further comprise a removable sheath. Preferably, the sheath is made of a flexible material and wraps fully or partially around the device. The sheath can be made of any biocompatible, flexible material such as a polymer or a rubber, e.g. polyester or silicone or polyurethane or other. Advantageously, the sheath can protect the device and avoid the deployment of the anchor members until needed. The piercing of unintended tissues and other objects can thus be avoided. The deployment (popping-out') of the anchor members can be initiated either through removal of the sheath, by bending the elongate body, or using the shape memory effect of a shape memory material such as Nitinol. The anchor member may be biased to the deployed position (i.e. an extended state where it extends away from the contact surface) and be held in the undeployed state (e.g. substantially flush with the contact surface) by the sheath so that removing the sheath causes the anchor members to extend away from the contact surface.

The device can further comprise a contracting means for contracting the length of the elongate body. When the elongate body is a tube, the contracting means may include a wire, or the like, extending through the tubular elongate body. The wire can be manipulated to reduce the length of the elongate body and bring the two free ends of the implant closer to each other. In a preferred embodiment, the wire is pulled when the device is in a circular or ring-like configuration and is attached to soft tissue such as a mitral annulus in order to reduce the diameter of the device and hence the annulus. Alternatively, the contracting means may extend along the outside of the elongate body and be moveably attached thereto, such as by means of the anchor members or by any other suitable means. The contracting means may be connected to a tool for positioning the device, such that the contracting means is manipulated by the tool. The contracting means may include a locking clip to tighten and/or to cut separate the contracting means from any other hardware such that the contracting means remains around the device in situ. The wire may be of any suitable material, such as nylon.

In one embodiment, the device further comprises a tool for positioning the device in order to penetrate the soft tissue. The tool may also be used to deliver the device to the implantation site, to support the device, and/or to reconfigure the device between linear and curved configurations. An example of such a tool is described below.

From yet another aspect, there is provided a device for supporting heart tissue, the device comprising an elongate body having at least one compliant portion and at least one anchoring portion, wherein the at least one anchoring portion comprises anchor members for penetrating the heart tissue, the anchor members extending in substantially the same direction along the elongate body. Advantageously, the anchor members can move between an undeployed position and a deployed position in which they protrude away from a surface of the elongate body. The anchor members can be deployed by removing a sheath surrounding the device, by bending the device, by heat/moisture activation, or the like.

In use, the device is delivered to a soft tissue implantation site, the anchor members deployed, and the device moved against the soft tissue substantially in the direction of the free ends of the anchor members to attach the device to the soft tissue. The device can be re-shaped/re-sized at the soft tissue implantation site, and/or re-shaped/re-sized after attaching to the soft tissue. A preferred use of the device, as defined above, is for supporting heart tissue. The heart tissue may be a mitral annulus for mitral valve repair. The device can be used to attach to the annulus and contract the annulus in order to bring together valves depending from that annulus.

There is also provided a method for implanting a device for supporting soft tissue at an implantation site, the method comprising providing the device at the implantation site in a first position, bending the device to deploy the anchor members, penetrating the soft tissue with the anchor members and rotating the device relative to the soft tissue to fully anchor the device in the soft tissue. The method can further comprises contracting the device.

From yet another aspect, there is provided a tool for positioning a device, such as embodiments of the device described above, at an implantation site for supporting soft tissue at the implantation site, the tool comprising a body for supporting the device, the body being moveable between a contracted state and an expanded state. The body preferably has a substantially circular circumference which is larger in the expanded state than in the contracted state. The device is supported around this circumference, preferably at a central portion of the body.

The tool can be sized to fit within a catheter lumen i.e. the diameter of the tool and the body is less than a diameter of a catheter lumen. In this way, the tool itself can be delivered percutaneously to the implantation site, and then used to support and position a device for implantation at the implantation site.

The tool has a first end and a second end and the body is positioned between the first and second ends of the tool. The body can be defined by a plurality of struts extending between the first and a second ends, the struts being connected together at the first and the second ends. In the expanded state, the struts are splayed further apart near the central portion of the body compared to the ends of the body. The first end of the tool is intended, in use, to contact the soft tissue or a cavity defined by the soft tissue. The second end is connectable to a catheter or to a handle. Advantageously, body fluids can flow between the struts for minimal disruption at the implantation site.

The tool can be made from any suitable biomaterial. The body requires a suitable degree of flexibility in order to transition between the contracted and expanded states. In one embodiment, the struts defining the body are made from a shape memory alloy, such as Nitinol. The tool can be made from a single piece by cutting, such as by laser, a hollow cylinder of Nitinol to form the struts. Alternatively, struts can be made from flat Nitinol wires and joined together at the first and second ends. The struts can be manufactured so as to have an initial outward bend in order to facilitate their splaying to the expanded state.

According to another embodiment, a wire pull is used. The tool further comprises a mechanism for moving the body between the contracted and expanded states. The mechanism can include a connecting means connected to a first end or a second end of the body for moving the first and second ends closer together to expand the body and further apart to contract the body. When the device is supported on the body, this has the effect of expanding and contracting the device. A rod is connected to the distal end of the tool. A pull force is applied to increases tool diameter while a pushing force decreases tool diameter. In the preferred embodiment where the body is defined by struts or splay elements, moving the first end of the struts closer to the second end causes the struts to splay outwardly. The mechanism may also include an actuating means for moving the connecting means, such as a lever, trigger or handle.

The connecting means may alternatively comprise a central shaft (e.g. a thin solid cylinder) extending between the first and second ends and connected to the first end of the body and the cap, but in sliding relation to the body second end. In this embodiment, the shaft (and hence the body first end) is moveable in relation to the body second end. Therefore, pulling the shaft away from the first end will move the first end of the body closer to the second end of the body, thereby expanding the circumference of the body. The shaft can be actuated by any suitable means, such as manually or using a lever, handle, screw, catheter or the like. Advantageously, the second end of the tool is adapted to fit onto or into a distal end of a catheter. In this way, the tool is attachable to a catheter or the like. When in the contracted state, the body can be delivered through a lumen of the catheter to the implantation site. Once in position, the body can be expanded and support the device to be implanted.

Alternatively, the device can be attached to the body of the tool by adhesive, sutures, wires or the like, which can be removed in situ.

The tool can further comprise a contracting means for acting on a device supported on the body in order to change the length or configuration of the device. The contracting means can be a wire connected to the tool or to the mechanism for shortening the device length once the device has been implanted.

From a yet further aspect, there is provided use of a tool, as defined above, for delivering a device percutaneously to a implantation site, for supporting device to re-shape or re-size the device, or for imparting a torque on a device.

Advantages of the device and the tool of the present invention include ease of manufacture, a single-shot insertion with annulus stabilization, full annuloplasty performed percutaneously to reduce the whole perimeter (anterior and posterior), fast procedure, better accuracy in positioning and more control over implantation. Furthermore, the device can adapt to different size annuli.

BRIEF DESCRIPTION OF THE DRAWINGS

Further aspects and advantages of the present invention will become better understood with reference to the description in association with the following in which.

DETAILED DESCRIPTION OF THE INVENTION

Figure 1A:
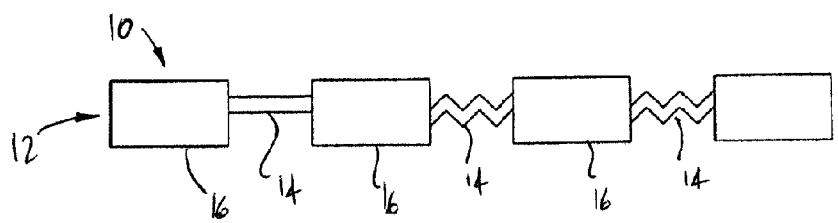
FIGS. 1a and 1b illustrate a device according to an embodiment of the present disclosure, the device including anchoring and compliant portions.

A first embodiment of a device 10 for supporting soft tissue is schematically illustrated in FIG. 1, in which the device 10 comprises an elongated body 12 having at least one compliant portion 14 and at least one anchoring portion 16. Reference is made to "device", but the device 10 may also be described as an implant, among other names. The length of the elongate body 12 can be adjusted by compressing or expanding the compliant portion 14. Also by means of the compliant portion 14 and/or the anchoring portion 16, the elongate body 12 can be bent so as to be configurable between a linear configuration and a shaped configuration, such as a ring-like shape (e.g., circular shape, C shape, D shape, arcuate shape, saddle shape, etc). In this way, the device 10 can be placed into an appropriate shape or form to be anchored into the soft tissue to support the soft tissue and adjust its dimensions and shape. The compliant portion 14 is thus compliant under bending, with compression/expansion capability.

In the embodiments illustrated herein, the device 10 is used to anchor into heart tissue such as a mitral annulus, to reduce a diameter thereof for mitral valve repair. The device 10 can be attached to the annulus to re-shape and/or re-size the annulus in order to bring closer valve leaflets that are supported by that annulus. It will be appreciated that embodiments of the device 10 described herein can enjoy other uses within the scope of the present disclosure.

According to an embodiment, the elongated body 12 is tubular and may have a diameter small enough to allow delivery of the device 10 through a catheter lumen. The elongated body 12 comprises a plurality of the compressible and anchoring portions 14 and 16, said portions being alternately positioned along the length of the elongate body, although other configurations and sequences are possible (e.g., other than a 1:1 alternating sequence).

Figure 1B:
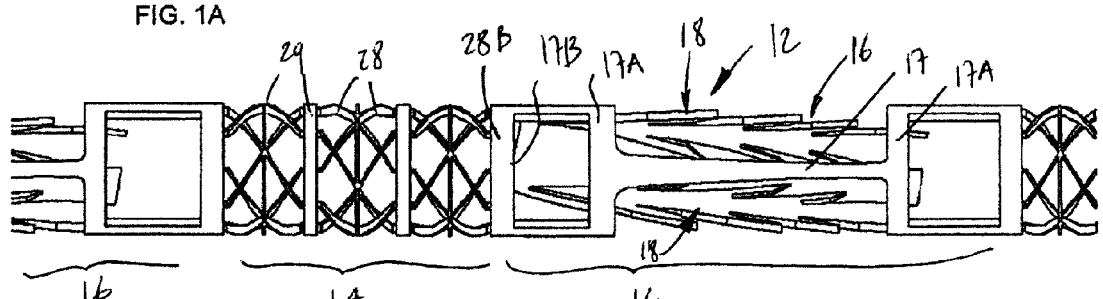
Figure 2A:
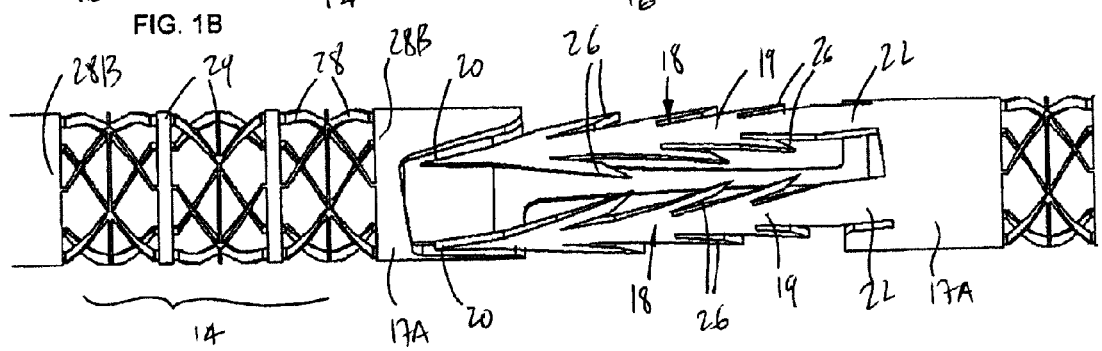
FIGS. 2a and 2b illustrate an example of the anchoring portions of the device of FIG. 1.
Figure 2B:
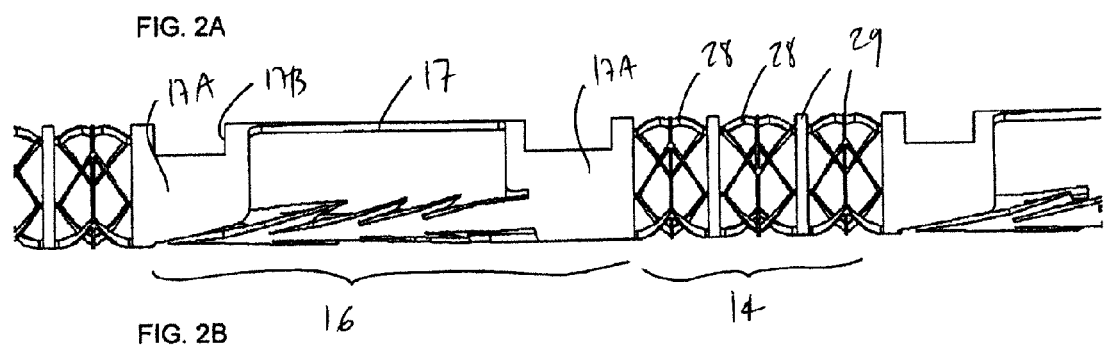

As best seen in FIGS. 2a and 3a, each anchoring portion 16 has one or more struts 17 and one or more anchor members 18. The struts 17 extend between tubular bands 17A on opposite ends of the anchoring portions 16 (with openings 17B optionally in the bands 17A for subsequent installation). The anchor members 18 each have a finger 19 with a free end 20 for protruding and penetrating into the soft tissue in use and a base end 22 moveably connected to the elongated body 12. The free end 20 is narrower than the base end 22 to facilitate piercing the soft tissue, and the illustrated embodiment shows a pointy shape for the free end 20. The anchor members 18 are arranged along the elongated body 12 to be oriented in relation to the elongate body in substantially the same direction. In other words, the anchor members 18 generally point in the same direction when the elongated body 12 is in its linear configuration, as in FIGS. 1b, 2a and 2b. In FIGS. 1b, 2a and 2b, the plurality of anchor members 18 are arranged in rows along a contact surface of the elongate body 12, i.e., the surface of the elongated body 12 that will be against the soft tissue when the elongated body 12 is deformed into a ring-like shape. This arrangement may facilitate anchoring of the device 10 to the heart tissue in that the anchor members 18 can be caused to penetrate the heart tissue at substantially the same time. As described hereinafter, the anchor members 18 can also be raised from the elongate body 12 or be slanted at any angle relative to the elongate body 12 when the elongated body 12 is in its shaped configuration.

Figure 3:
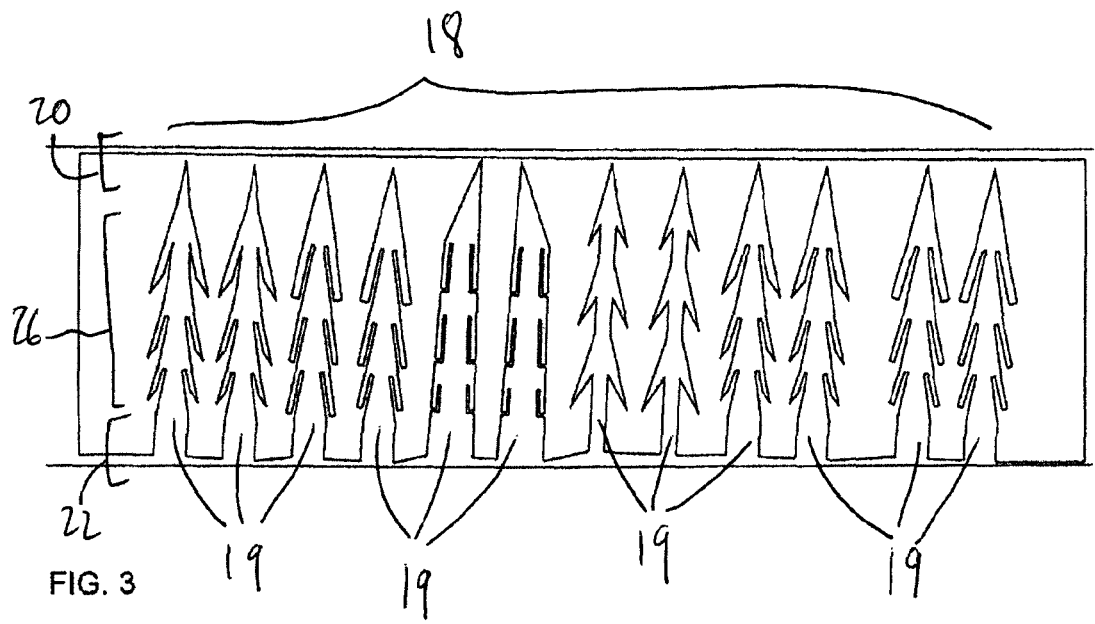
FIG. 3 illustrates different embodiments of anchor members on the anchoring portions of the device of FIG. 1.

The anchor members 18 may further include retaining elements 26 between the ends 20 and 22, for better grip of the anchor member 18 in the soft tissue. The retaining elements 26 are similar to chevrons mounted to the finger 19, and pointing in the same direction as the pointy free end 20. Hence, the anchor members 18 of the device 10 have a fir tree-like shape, with the combination of the pointy free end 20 and the retaining elements 26. As shown in FIG. 3, the anchor members 18 can have numerous other shapes, and FIG. 3 provides a few examples of many possible shapes. For instance, the retaining elements 26 can be in the form of a protrusion, a barb, an opening or the like. The anchor members 18 with such retaining elements 26 can act similar to fish hooks in order to assist retention of the device 10 in soft tissue. The anchor members 18 can take any suitable form or shape other than those illustrated in the figures or described therein.

Figure 7:
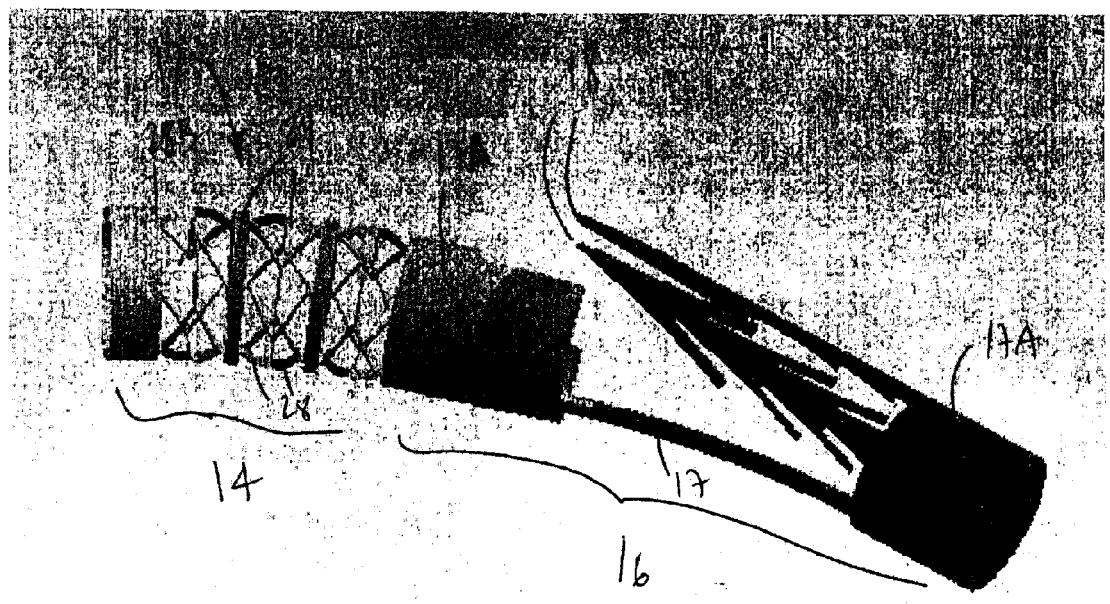
FIG. 7 illustrate the device of FIG. 1 as shaped to expose anchoring members.
Figure 8A:
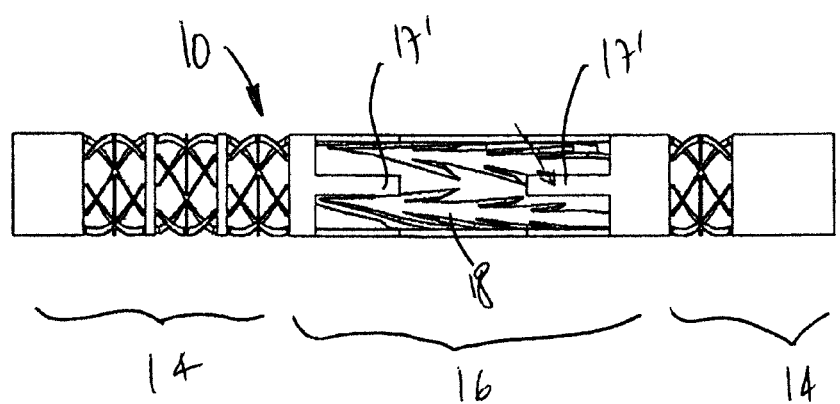
FIGS. 8a and 8b illustrate other embodiments of the device of the present disclosure for use with a deployment tool.
Figure 8B:
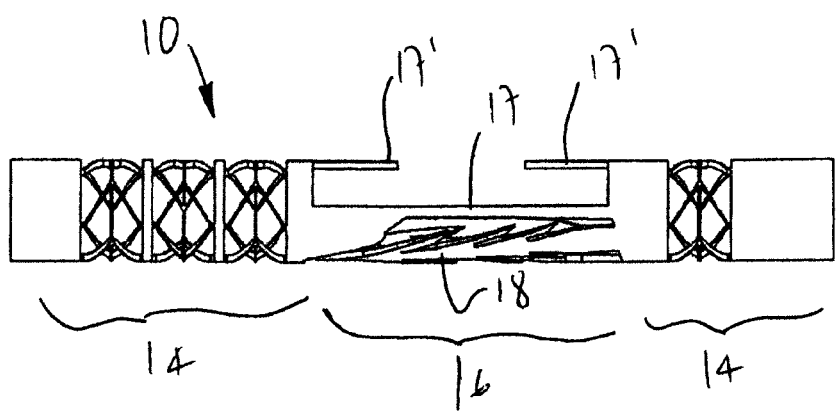

The anchor members 18 can move between an undeployed orientation (see for example FIGS. 1a-2b) and a deployed orientation (see for example FIG. 7). In the undeployed position, the anchor members 18 are tucked within the cylindrical periphery of the elongated body 12, with the elongated body 12 being in its linear configuration. In the deployed orientation, the free end 20 of the anchor members 18 protrude away from a remainder of the elongated body 12 and are thus exposed to penetrate the soft tissue in use. The deployed orientation can be initiated by shaping the elongate body 12, for example into a partial or complete ring shape. In doing so, the struts 17 deform from their linear shape into a curved shape, for instance by plastic deformation of the struts 17. This causes the anchor members 18 to 'pop-out', i.e., extend away from the ring-shape of a remainder of the elongated body 12. As seen in FIG. 7, the anchor members 18 protrude circumferentially along a direction defined by a vector having a component being at least tangential to a plane of the elongated body 12 arranged in the ring-like shape, the plane being one in which the whole of the ring-shaped elongated body 12 lies. In other words, the anchor members 18 are exposed radially outward of the ring-shaped elongated body 12. Hence, a rotation of the ring-shaped elongated body 12 about its center may cause a penetration of the anchor members 18 into surrounding soft tissue, with the pointy end 20 and retaining members 26 penetrating the soft tissue.

Figure 4:
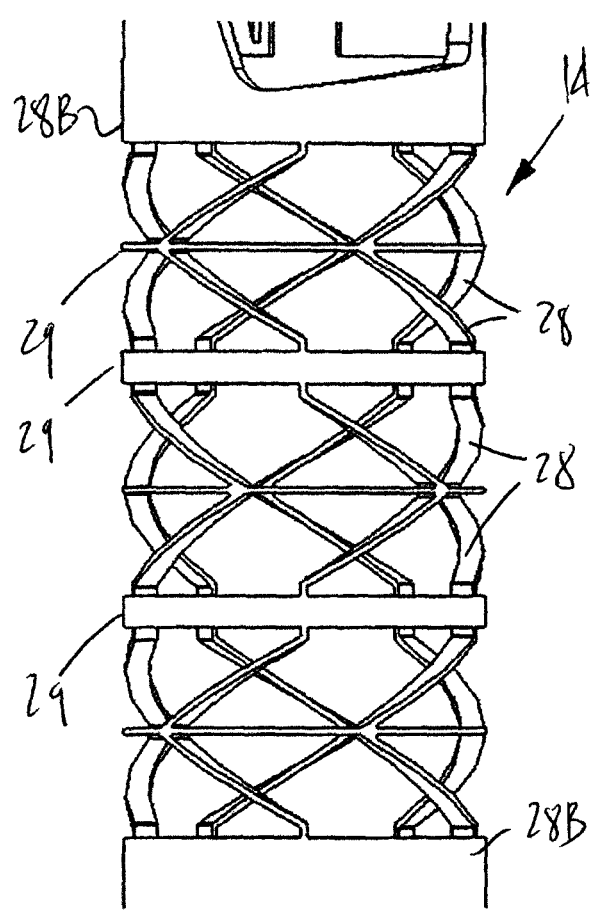
FIG. 4 illustrates the compliant portion of the device of FIG. 1.
Figure 5:
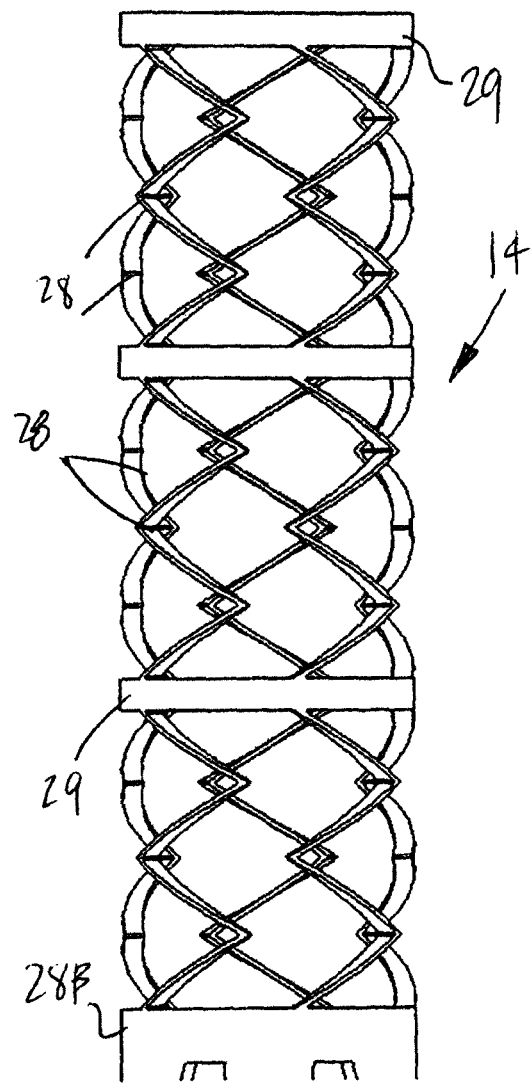
FIG. 5 illustrates an alternative embodiment of the compliant portion of FIG. 1.
Figure 6:
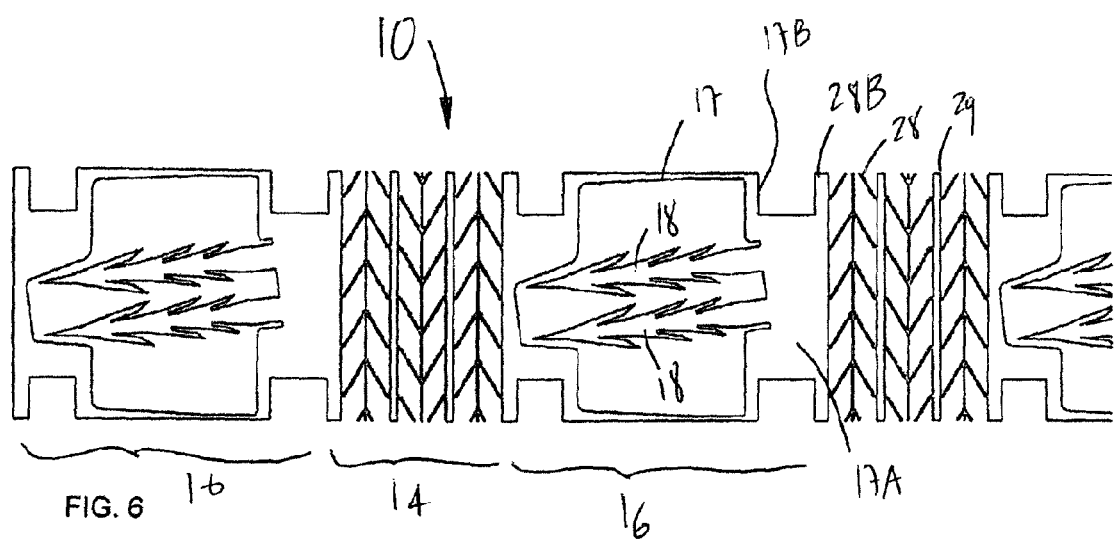
FIG. 6 illustrates a single cutout sheet prior to being formed in to the device of FIG. 1.

Referring to FIGS. 4 and 5, each compliant portion 14 comprises at least one deformable member 28 (e.g., flexible, bendable, shapeable in elastic or plastic deformation) between tubular bands 28A (which may be common to that of the anchoring portions 16). The at least one deformable member 28 may consist of a longitudinal strip(s) of material or wire, for example arranged in an undulating pattern of material (i.e., non-straight, with some back and forth pattern), with or without transverse rings 29 or any other suitable shape or form to allow deformation thereof, by lengthening/shortening and curving. The rings 29 may increase the strength of the compliant portion 14 to cause a joint deformation of the compliant portions 14 and anchoring portions 16 (at the struts 17). The strips in the undulating pattern of material should be interpreted as being sinusoidal or sinusoidal-like, wavy, zigzag, or of similar shapes. Many different permutations of the arrangement of the compliant portions 14 and anchoring portions 16 on the elongated body 12 are possible. Therefore, when the elongated body 12 is shaped into a ring-like figure, the complaint portions 14 and/or the struts 17 of the anchoring portions 16 may contribute in the body 12 reaching its appropriate ring-like shape. In the process, the anchor members 18 may project out of the ring-like shape, at least in a tangential direction relative to the ring. It is also observed that the elongated body 12 is tubular and therefore defines a lumen by which the device 10 may be moved along a guidewire. In the implant 10, the dimensioning of the deformable member 28 of the compliant portion 14 is selected as a function of the dimensioning of the struts 17 of the anchoring portions 16. The object is to have the whole of the elongated body 12 deform to the ring-like shape, and it is hence desired to have both the compliant portions 14 and the anchoring portions 16 react in similar fashion to bending moments on the elongated body 12. In other words, this may help in having the anchoring members 18 protrude in the manner described above.

Although not shown the device 10 can further comprise a removable sheath made of a flexible material and wraps fully or partially around the device 10. The sheath is made of any biocompatible, flexible material such as a polymer or a rubber, e.g. polyester or latex. The sheath protects the device 10 and avoids the deployment of the anchor members 18 until needed. The deployment ('popping-out') of the anchor members 18 can be initiated through removal of the sheath and/or by bending the elongated body 12.

Although not shown, the device 10 can further comprise a contracting means for contracting the length of the elongate body 12 via deformation of the compliant portions 14. The contracting means can be a wire extending through or along the elongate body which can be manipulated to reduce the length of the elongate body. Other types of contracting means are also possible.

Figure 10:
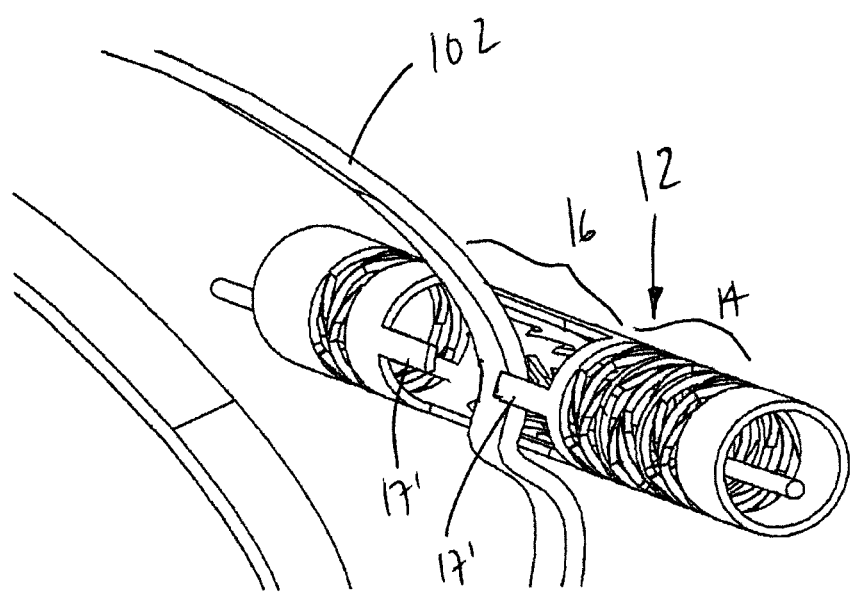
FIG. 10 illustrates an interrelation between the device of FIGS. 8a and 8b and the deployment tool of FIG. 9.

In one embodiment, the device 10 is a single cutout of a tube or of a sheet of Stainless Steel 316L which is laser cut to form the compressible and anchoring portions. Any other suitable biomaterial may be used. Preferably, the compliant portions 14 can deform elastically or plastically to change the dimensions of the implant 10 by through the use a reasonable force (for example 5-15 Newtons). In FIG. 10, there is illustrated the device 10 prior to being shaped or imprinted into a tube to reach the linear configuration of FIGS. 1a and 1b. Suitable materials include, but are not limited to, stainless steel 316L, titanium or titanium alloys, such as Nitinol or Ti—Al—V, cobalt chromium alloys, other metallic alloys, polymers, composites. In a preferred embodiment, the device is a single tube of Stainless Steel 316L which is laser cut/etched to form the compressible and anchoring portions. Alternatively, the device can be made from different components/materials joined together. Also, the device or parts of the device can have a coating for promoting cell growth to aid fixation of the device to the tissue and for improving biocompatibility.

In one embodiment in which it is used for mitral valve repair, the device 10 is about 10.0 cm long when in its elongated configuration, but may be of a length ranging between 7.0 and 13.0 cm long. This length range includes the approximate average circumference of a sick mitral annulus minus the distance from trigone to trigone which amounts to around 2 cm. When the device 10 is compressed, the length can reduce to about 7 centimeters. The diameter of the device 10 should be small enough to fit within a catheter lumen but wide enough to retain satisfactory mechanical properties. In one embodiment in which it is used for mitral valve repair, the device 10 has an outer diameter of about 3.0 mm (0.118"), although a range if 2.0 mm to 4.0 mm could be suitable in such conditions. In one embodiment, the anchor members 18 occupy most of a contact area between the implant 10 and the heart tissue. Each anchoring portion 16 may comprise 2 or 3 anchor members 18, although more or less could also be used. This is estimated to be between about 40 to 60 percent of the circumference of the device 10 at the anchoring portions 16. The anchors can be about 0.5 to 1.5 mm wide and have a length between about 6.0 to 12.0 mm.

In another embodiment, the device 10 is at least partially made from a shape memory alloy such as Nitinol which allows deployment of the anchor members 18 through temperature change activation.

In use, the device 10 can be delivered percutaneously, or in any other manner, to the desired implantation location in situ through a catheter lumen while in a substantially linear state, along a guidewire which has C or circular shape at its end. The elongated body 12 may then be shaped into the ring-like shape to match the soft tissue to which the device 10 will be anchored. The shaping the elongated body 12 also deploys the anchor members 18 such that they protrude circumferentially along a direction defined by a vector having a component being at least tangential to the plane or curve of the ring-like shaped elongated body 12. A position and/or orientation of the device 10 is then adjusted relative to the heart tissue, for the subsequent anchoring of the device 10 to the soft tissue. In the case of a mitral valve, the implant 10 in its ring-like shape is positioned along the annulus. The implant 10 in its ring-link shape may then be rotated for the implant 10 to move along the annulus, with the anchoring members 18 penetrating into the soft tissue of the annulus. The elongated body of the device 10, now anchored to the annulus, can then be re-sized or re-shaped in order to re-size or re-shape the annulus. In one example, the device 10 is bent into a 'C' shape and is anchored to the annulus by rotating it, about its center which engages simultaneously all anchors into tissue. Once anchored, the free ends of the device 10 are brought together to form a closed or open ring by contracting means and are fixed in that arrangement.

Referring now to FIGS. 8a, 8b, 9 and 10, a tool 100 is provided for implanting the device as described in any of the embodiments of the device described above, at an implantation site. The device 10 shown in FIGS. 8a and 8b has a segmented strut, with strut segments 17' separated by a gap. The tool 100 may also be used to position and deliver any other device. The tool 100 may thus be used to deliver the device 10 percutaneously to the implantation site, to support the device 10 and assist in anchoring the device 10, to shape the device 10 between the linear and shaped configurations, and to provide a rotational movement to the device 10 in order to anchor it to the surrounding soft tissue.

Figure 9:
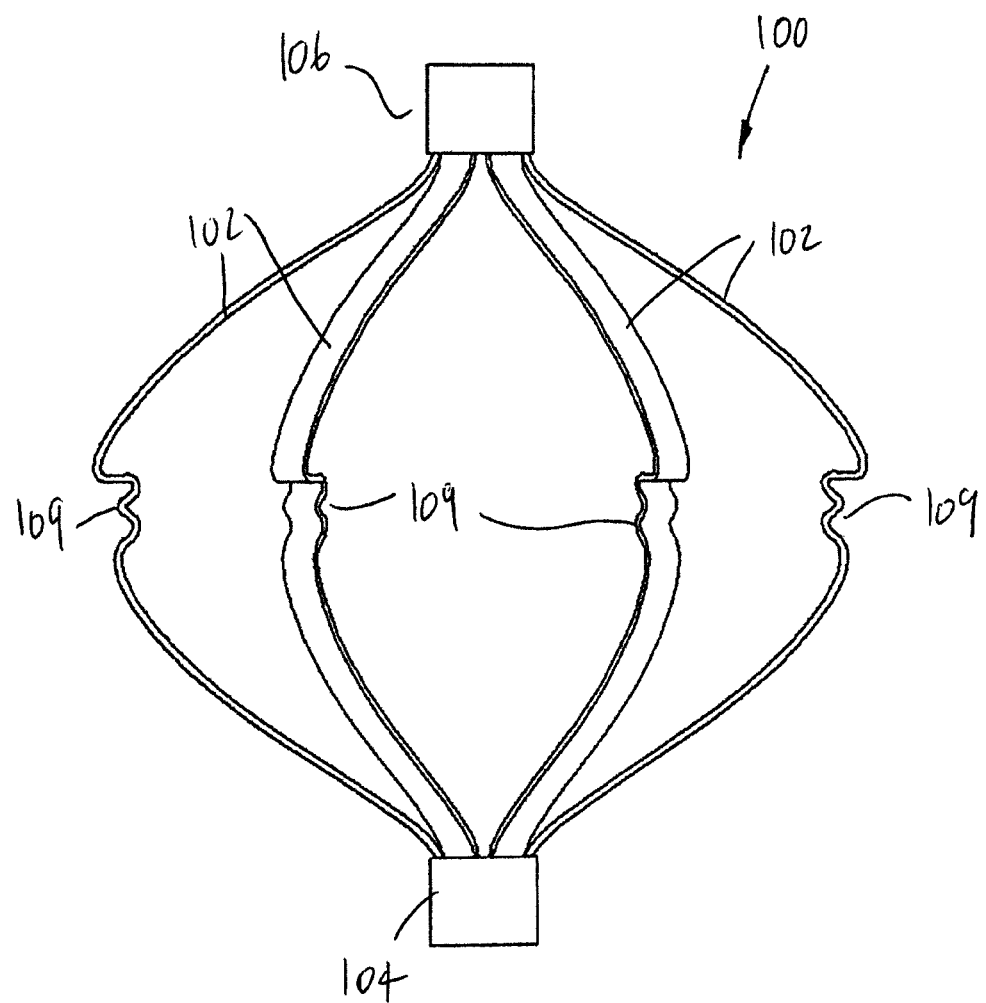
FIG. 9 illustrates struts of a deployment tool.
Figure 13:
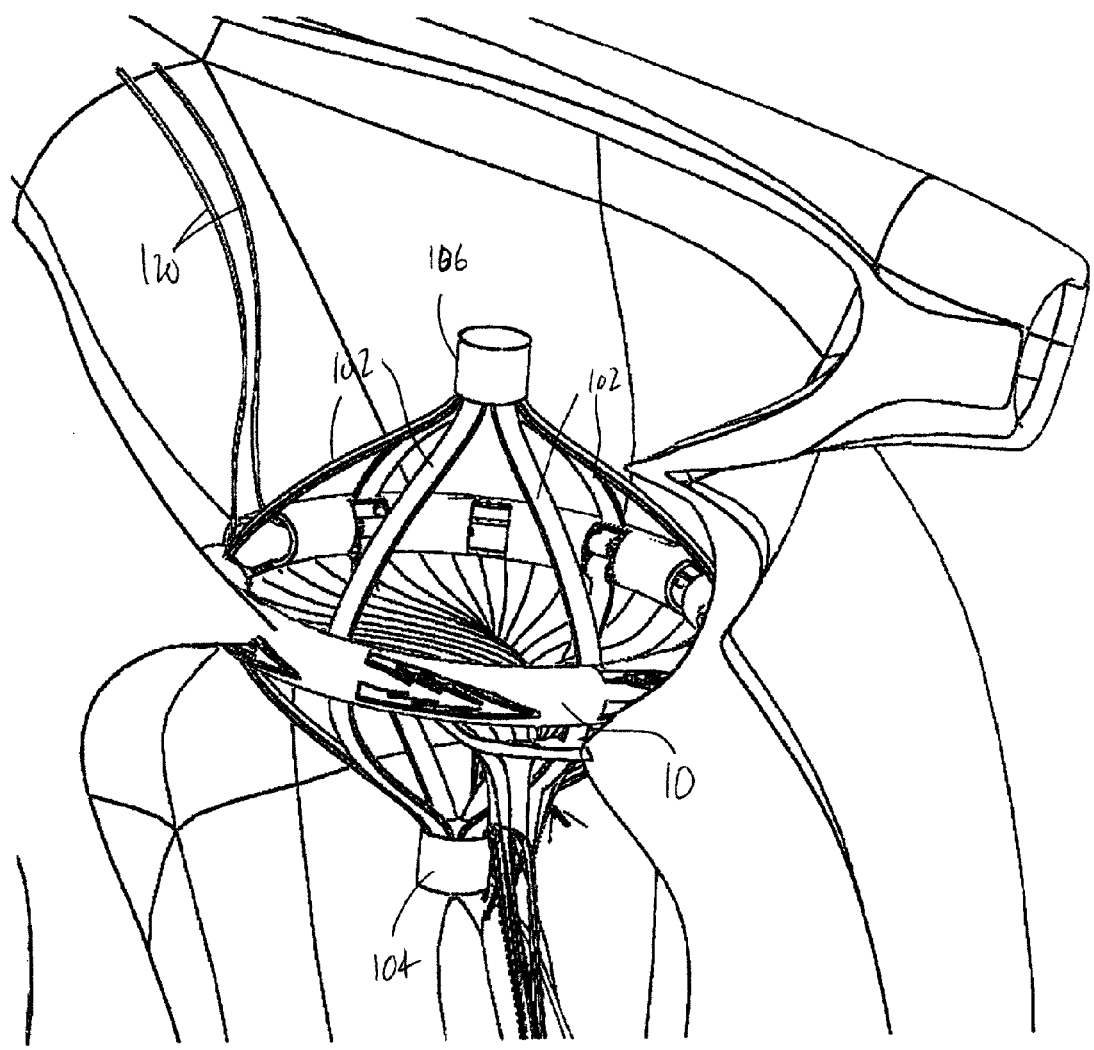

The tool 100 is moveable between a contracted state and a deployed state as in FIGS. 9, 10 and 13. Partially deployed states are also possible. The tool 100 has a substantially circular circumference which is larger in the deployed state than in the contracted state. The device 10 can be supported around this circumference, preferably at a central portion of the tool 100. The tool 100 is defined by a plurality of struts 102 extending between first and second ends 104, 106 of the tool 100, the struts 102 being connected together at the first and the second ends. In the deployed state, the struts 102 are splayed further apart near the central portion of the tool 100 compared to the ends of the tool 100. The first end 104 of the tool 100 is intended, in use, to contact the soft tissue or a cavity defined by the soft tissue. The second end 106 is connectable to an internal catheter (not shown). As shown, the struts 102 can be suitably shaped to define a channel 109 for receiving the device 10 in its ring-like shape. As the interconnection between device 10 and tool 100 may be done percutaneously, it is contemplated to provide both of them with radio-opaque markers.

The tool 100 may be sized to fit within an external catheter lumen (not shown) so that the tool itself, together with the device 10, can be delivered percutaneously to the implantation site, and then used to support and position the device 10 for implantation at the implantation site. The tool 100 can be made from a single piece tube by cutting, such as by laser, to form the struts as best seen in FIG. 21. Any suitable material can be used, such as Nitinol. The struts 102 are processed so as to have an initial outward bend in order to facilitate their splaying to the expanded state.

The tool 100 further comprises a mechanism (now shown) for expanding/contracting between the contracted and deployed states. In one embodiment, the mechanism includes a connecting means connected to the first end 104 or to the second end 106 of the tool 100 for moving the first and second ends 104, 106 closer together to expand the tool 100 by deformation of the struts 102 and bring the device 10 into contract with the surrounding soft tissue. When the device 10 is supported on the body, this has the effect of expanding and contracting the device 10, notably by the struts 102 being held releasably captive by the strut segments 17' of the device 10 of FIGS. 8a and 8b (or in openings 17B as in FIG. 1b). The mechanism may thus include an actuating means for moving the ends 104, 106 together, such as a lever, trigger or handle. In use, when the tool 100 has been delivered percutaneously to the implantation site, the actuating means are positioned outside of the patient's body for manipulation by a medical practitioner.

Referring now to FIGS. 11-14, in use, the device 10 and tool 100 can be used for percutaneous mitral valve repair. The tool 100 can be used in a number of ways. For example, the device 10 can be attached to the tool 100 before placing the tool at the implantation site and the device delivered to the implant site at the same time that the tool is deployed (moved from the contracted state to the expanded state). In other words, the deployment of the device and the tool 100 is simultaneous. Alternatively, the tool 100 can be deployed first and positioned around the annulus, and then the device delivered through the tool 100 to the implantation site.

Figure 11:
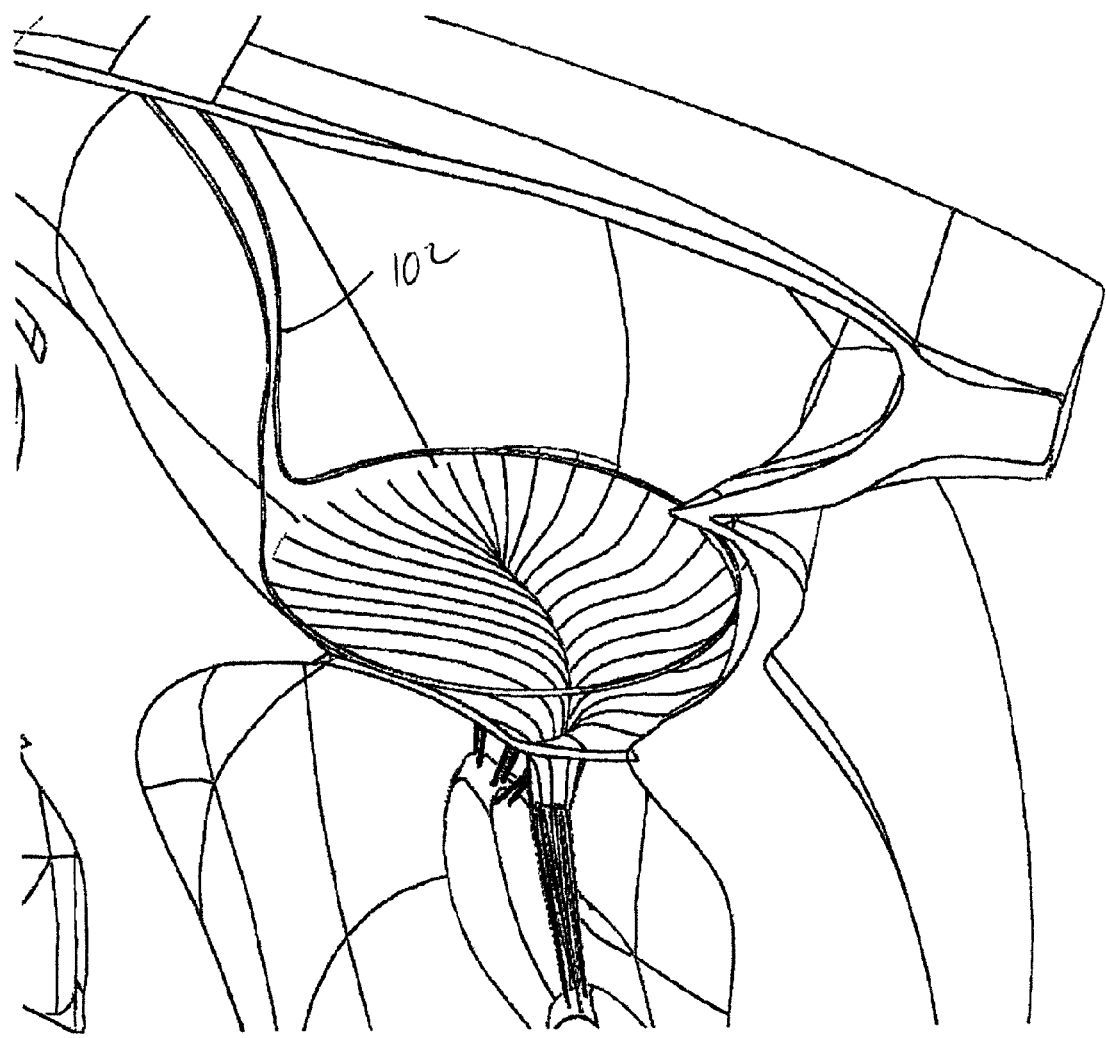
FIGS. 11 to 14 illustrate different steps to anchor the device of the present disclosure to soft tissue using the deployment tool, according to an aspect of the present disclosure.
Figure 12:
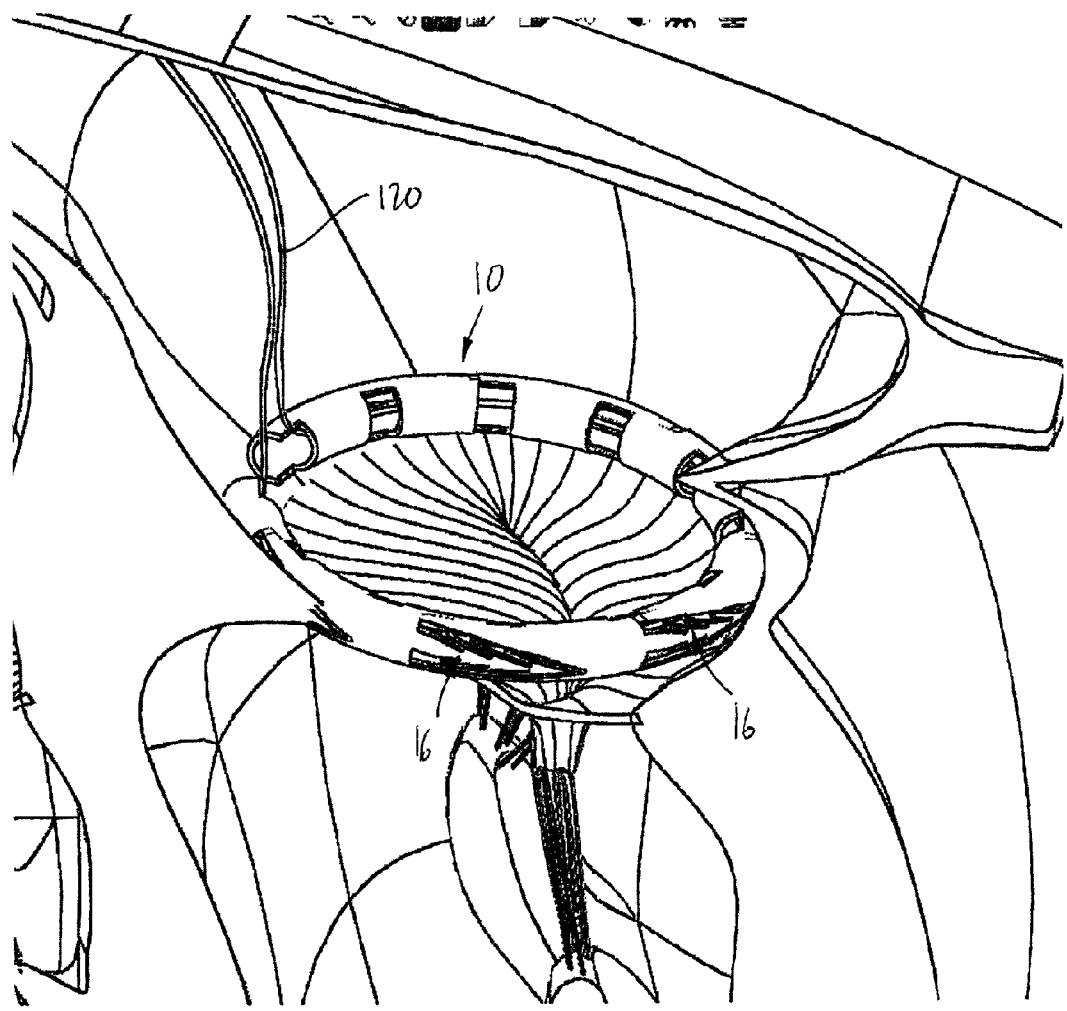
Figure 14:
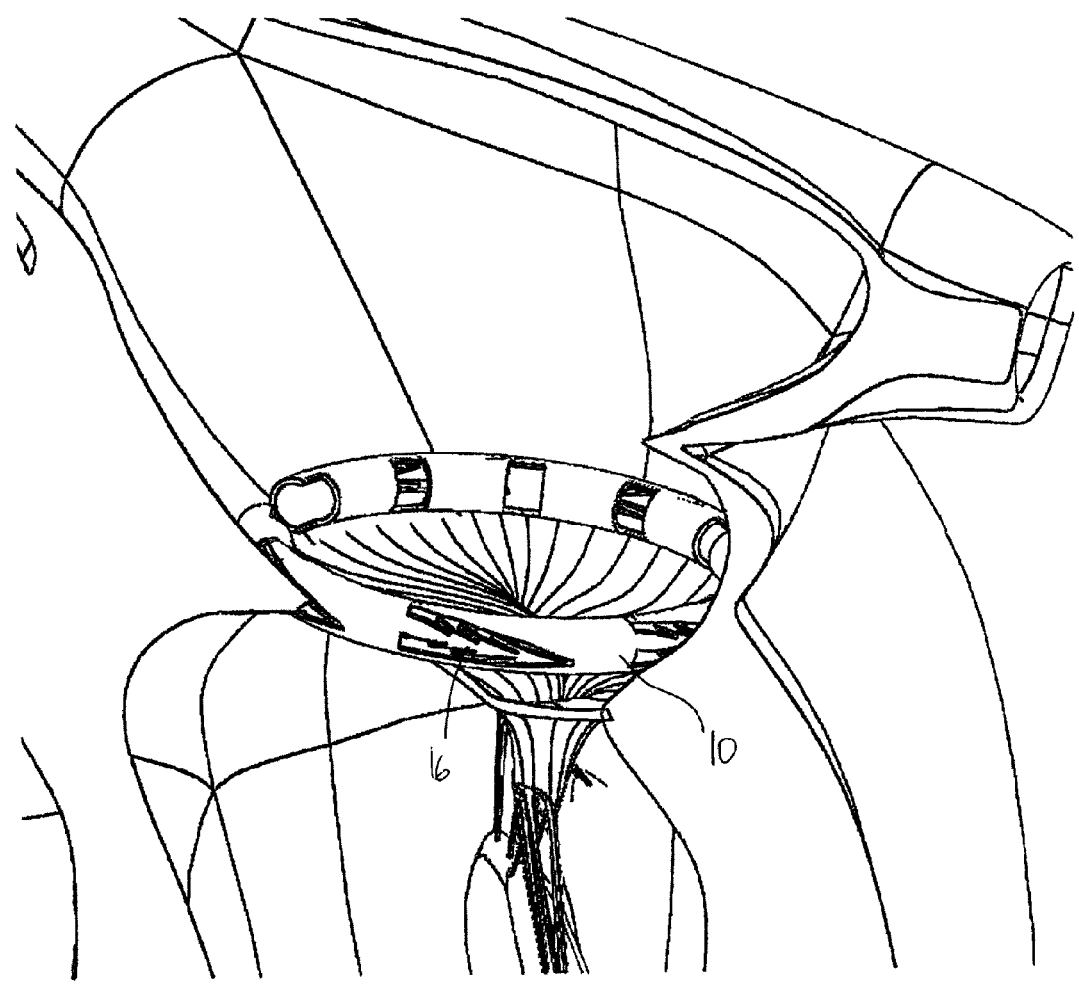

In one embodiment, referring to FIG. 10, a guidewire 120 is inserted from the femoral vein to reach the left atrium. The guidewire 120 forms a loop surrounded by the annulus. Referring to FIG. 11, the device 10 may be placed onto the loop of the guidewire 120, in the process shaping into the ring-like shape. In the manner described above. This may be done by advancing a catheter over the guidewire 120 until the left atrium and the implantation site is reached. Referring to FIG. 13, the tool 100 in the contracted state is advanced as one unit (for instance through the outer catheter) until the first end 104 of the tool 100 reaches the atrium. The tool 100 is then positioned such that the tool first end 104 is received within the mitral valve annulus, with the channels 109 in the struts 102 being aligned, for instance as guided by imagery and radioopaque markers on the struts 102 and device 10. The struts 102 of the tool 100 are then caused to splay outwardly (extended state) and into engagement with the device 10, for instance in the manner shown in FIG. 10. It is pointed out that frictional forces between the struts 102 and the device 10 may suffice to rotate the device 10. According to an embodiment, the guidewire may be restricted to a certain size when the deployment tool 100 is expanded, whereby the struts 102 apply a radial force on the implant 10 and in turn transmit torque. The tool 100 engaging the device 10 is then rotated, for instance by about 5°, which in turn rotates the device/implant 10, thus causing a penetration of anchor members 18 of the device 10 into the annulus tissue to anchor the device 10 securely into the tissue. Referring to FIG. 14, the tool 100 and guidewire 120 may then be removed. In removing the guidewire 120, a dimension of the device 10 is adjusted, for instance to reduce a diameter of the annulus and repair the mitral valve. Other tools may be used to reduce the dimensions of the device 10. The ends of the device 10 may be fastened together in any appropriate way to ensure that the device 10 maintains its shape and dimensions.

It should be appreciated that the invention is not limited to the particular embodiments described and illustrated herein but includes all modifications and variations falling within the scope of the invention as defined in the appended claims.

The invention claimed is:

1. A device for supporting soft tissue, the device comprising:
an elongated tubular body comprising a longitudinal sequence of compliant portions and anchoring portions,
the anchoring portions each comprising a single tube defining a contact surface for contacting soft tissue in use and at least one anchor member formed integrally in the contact surface by cutting or etching of portions of the contact surface around the at least one anchor member, the at least one anchor member being adapted to penetrate into soft tissue,
the compliant portions each comprising at least one deformable member extending between ends of the compliant portion, at least one of a distance and orientation between said ends being adjustable by application of a force on the elongated tubular body;
the elongated tubular body being deformable between first and second configurations, the second configuration being reached from the first configuration at least by deformation of at least one of the compliant portions, wherein, in the first configuration, the tubular body is rectilinear and defines a body longitudinal axis and the anchor members extend longitudinally parallel to the body longitudinal axis and are confined in the single tube, and, in the second configuration, the elongated tubular body has a circular shape and the anchor members of the anchoring portions protrude circumferentially and tangentially from the circular shape of the elongated tubular body for allowing the at least one anchor member to penetrate the soft tissue.

2. The device according to claim 1, wherein the at least one anchor member has a finger having a free end for protruding into the soft tissue in use and a base end connected to a remainder to the single tube.

3. The device according to claim 2, wherein the anchor member is shaped as a fir tree, with the free end having a pointy shape, and retaining members projecting laterally from the finger.

4. The device according to claim 1, comprising at least two of said anchor members for each of said anchoring portions.

5. The device according to claim 1, wherein the anchoring portions each comprise tubular bands at opposite ends, and at least one deformable strut between the tubular bands, the at least one anchor member projecting from one of said tubular bands.

6. The device according to claim 1, wherein the elongated tubular body comprises a plurality of the compliant portions and a plurality of the anchoring portions, said compliant portions and anchoring portions being alternately positioned along the length of the elongated tubular body.

7. The device according to claim 1, wherein the at least one deformable member is a longitudinal strip of undulating pattern.

8. The device according to claim 7, further comprising a plurality of the longitudinal strip extending along the compliant portion, and at least one ring transversely connecting the plurality of longitudinal strips and tubularly aligned with the elongated tubular body.

9. The device according to claim 1, wherein the elongated tubular body has a length ranging between 7.0 and 13.0 cm.

10. The device according to claim 1, wherein the elongated tubular body has a diameter ranging between 2.0 and 4.0 mm in the first configuration.

11. The device according to claim 1, wherein in the second configuration, the at least one anchor member is coplanar with the elongated tubular body.

* * * * *